United States Patent
Yoon

(10) Patent No.: US 6,248,088 B1
(45) Date of Patent: *Jun. 19, 2001

(54) METHODS FOR PERFORMING ENDOSCOPIC PROCEDURES

(76) Inventor: InBae Yoon, 2101 Highland Ridge Dr., Phoenix, MD (US) 21131

( * ) Notice: Subject to any disclaimer, the term of this patent is extended or adjusted under 35 U.S.C. 154(b) by 0 days.

This patent is subject to a terminal disclaimer.

(21) Appl. No.: 08/125,892

(22) Filed: Sep. 24, 1993

Related U.S. Application Data

(60) Continuation of application No. 07/789,599, filed on Nov. 8, 1991, now abandoned, which is a division of application No. 07/556,081, filed on Jul. 24, 1990, now Pat. No. 5,074,840.

(51) Int. Cl.$^7$ .............................. A61F 13/20; A61B 1/00; A61B 19/00
(52) U.S. Cl. ........................... 604/11; 600/104; 600/572; 128/898
(58) Field of Search ............................... 604/11–18, 1–3; 606/191–200; 600/104, 114, 572; 128/898

(56) References Cited

U.S. PATENT DOCUMENTS

| | | |
|---|---|---|
| 616,672 * | 12/1898 | Kelling .................. 600/114 |
| 654,564 | 7/1900 | Dargatz . |
| 682,090 | 9/1901 | Lee . |
| 685,088 * | 10/1901 | Barlow ..................... 604/1 |
| 702,997 | 6/1902 | Pugh . |
| 716,040 | 12/1902 | Holt . |
| 1,523,943 | 1/1925 | Fowle . |
| 1,562,656 | 11/1925 | Park . |
| 2,524,195 | 10/1950 | Hoover . |
| 3,039,468 | 6/1962 | Price . |
| 3,095,877 | 7/1963 | Rowan . |
| 3,253,594 | 5/1966 | Matthews et al. . |
| 3,459,175 | 8/1969 | Miller . |
| 3,495,586 | 2/1970 | Regenbogen . |
| 3,557,794 | 1/1971 | Van Patten . |
| 3,683,915 | 8/1972 | Voss . |
| 3,790,432 | 2/1974 | Baron . |
| 3,833,003 | 9/1974 | Taricco . |
| 3,941,125 | 3/1976 | Drake . |
| 3,952,742 | 4/1976 | Taylor . |
| 4,027,673 | 6/1977 | Poncy et al. . |
| 4,043,338 | 8/1977 | Homm et al. . |
| 4,077,412 | 3/1978 | Moossun . |
| 4,192,300 | 3/1980 | Devers . |
| 4,328,804 | 5/1982 | Shimatani . |
| 4,335,720 | 6/1982 | Glassman . |
| 4,372,295 | 2/1983 | Heckele . |
| 4,421,504 | 12/1983 | Kline . |
| 4,535,773 | 8/1985 | Yoon . |

(List continued on next page.)

FOREIGN PATENT DOCUMENTS

| | | |
|---|---|---|
| 0278937 | 8/1988 | (EP) . |
| 0432363 | 6/1991 | (EP) . |

Primary Examiner—Dennis Ruhl
(74) Attorney, Agent, or Firm—Blank Rome Comisky & McCauley LLP

(57) ABSTRACT

A packing device for use in endoscopic operative procedures is formed of an elongate strip of absorbent, preferably expandable material having a rigid, dry state of a size to permit passage through a narrow endoscopic portal to an internal operative site and having a soft wet state when body fluids are absorbed thereby such that the packing device exposes and isolates tissue to be treated and protects adjacent tissue at the operative site while, in the dry state, is sufficiently rigid to manipulate tissue. A method of packing an internal operative site during an endoscopically performed procedures includes inserting a rigid strip of absorbent, preferably expandable, material through a narrow endoscopic portal and positioning the strip of material at the operative site such that at least a portion of the strip of material absorbs body fluids to become soft and pliable.

7 Claims, 3 Drawing Sheets

U.S. PATENT DOCUMENTS

| | | |
|---|---|---|
| 4,553,965 | 11/1985 | Conn et al. . |
| 4,573,964 | 3/1986 | Huffman . |
| 4,607,619 | 8/1986 | Seike et al. . |
| 4,608,965 | 9/1986 | Anspach, Jr. et al. . |
| 4,610,659 | 9/1986 | Friese . |
| 4,748,982 | 6/1988 | Horzewski et al. . |
| 4,822,332 | 4/1989 | Kajander . |
| 4,857,044 | 8/1989 | Lennon . |
| 4,895,559 | 1/1990 | Shippert . |
| 4,900,315 | 2/1990 | Lundqvist et al. . |
| 5,002,557 | 3/1991 | Hasson . |
| 5,007,895 | 4/1991 | Burnett . |
| 5,041,093 | 8/1991 | Chu . |
| 5,061,274 * | 10/1991 | Kensey ............................. 604/15 X |
| 5,074,840 | 12/1991 | Yoon . |
| 5,074,871 | 12/1991 | Groshong . |
| 5,113,846 | 5/1992 | Hiltebrandt et al. . |
| 5,188,630 * | 2/1993 | Christoudias ..................... 604/11 X |
| 5,192,300 * | 3/1993 | Fowler ............................. 604/15 X |
| 5,203,767 * | 4/1993 | Cloyd ............................... 604/15 X |
| 5,295,952 * | 3/1994 | Pietrafitta ............................. 604/1 |

\* cited by examiner

METHODS FOR PERFORMING ENDOSCOPIC PROCEDURES

This application is a continuation of application Ser. No. 07/789,599, filed Nov. 8, 1991, now abandoned which is a division of application Ser. No. 07/556,081, filed Jul. 24, 1990, now U.S. Pat. No. 5,074,840.

BACKGROUND OF THE INVENTION

1. Field of the Invention

The present invention pertains to medical packing and, more particularly, to packing devices and methods for endoscopically performed operative procedures.

2. Discussion of the Prior Art

Endoscopically performed operative procedures are preferred for surgery on the human body due to their least invasive nature and reduced trauma and tissue damage as compared with open surgery. There are many common endoscopically performed operative procedures including, for example, laparoscopy (pelviscopy), gastroentroscopy, laryngobronchoscopy and arthroscopy. While endoscopically performed operative procedures are preferred, there are obstacles to expanding endoscopy to include the various procedures currently performed with open surgery. One of the obstacles is that packing of the internal operative site has not been able to be accomplished in the past due to the fact that access to the operative site is available only through a narrow portal normally including a cylindrical sleeve positioned by means of a puncturing instrument. Without packing, endoscopic procedures are much more difficult and dangerous to perform, even with the use of instruments particularly useful in endoscopy, such as laser and electrosurgical instruments, since the tissue or organ structure cannot be adequately exposed and manipulated, the surrounding tissue and organ structure is not protected during the procedure and body fluids cannot be removed from the operative site without the use of expensive and cumbersome suction equipment.

There is a great need to expand the types of procedures that can be endoscopically performed in order to decrease trauma and recovery time for patients while simultaneously reducing medical costs. Accordingly, much effort has been expended in the development of endoscopic instruments for specific procedures; however, to date, no adequate system has been devised to permit packing during endoscopically performed operative procedures.

SUMMARY OF THE INVENTION

Accordingly, it is a primary object of the present invention to provide a packing device for use in endoscopically performed operative procedures to expand the types of procedures that can be performed endoscopically while increasing patient safety and exposure of operative sites in endoscopic procedures presently being performed.

Another object of the present invention is to form a packing device of an elongate strip of absorbable material having a rigid dry state allowing passage through a narrow endoscopic portal and permitting tissue manipulation and precise positioning at an internal operative site to expose tissue and organ structures to be treated, absorb body fluids and protect adjacent tissue and organ structures.

A further object of the present invention is to pack an internal operative site through a narrow endoscopic portal using a strip of absorbent material having a rigid, dry state prior to use and a soft flexible, wet state when exposed to body fluids.

Yet an additional object of the present invention is to endoscopically pack an internal operative site using a strip of absorbent material having a relatively straight configuration in a dry state and assuming a different, non-straight configuration in a wet state to allow the strip of material to have a predetermined configuration when positioned at the operative site to absorb body fluids.

Some of the advantages of the present invention over the prior art are that precise packing at an internal operative site is accomplished via a narrow portal thereby expanding the types of procedures that can be performed endoscopically and, further, increasing safety and efficacy in endoscopic procedures in general, that the packing device is rigid or stiff in a dry state to allow precise placement thereof as well as manipulation of tissue, that the packing device facilitates removal of infected fluids, such as pus, and abnormal fluids, such as cystic fluids, that the packing device serves as a culturing medium to identify specific infected organisms, that the packing device can apply medicaments to tissue, and that, when a plurality of packing devices are used in an endoscopic procedure, each packing device is individually identified externally to facilitate manipulation.

The present invention is generally characterized in a packing device formed of an elongate strip of absorbent, preferably expandable, material having a rigid dry state of a size to permit passage through a narrow endoscopic portal to an internal operative site and having a soft, flexible or rigid, wet state when body fluids are absorbed thereby. A method of packing an internal operative site during an endoscopically performed procedure includes inserting a rigid strip of absorbent, preferably expandable, material through a narrow endoscopic portal and positioning the strip of material at the operative site such that at least a portion of the strip of material absorbs body fluids to soften the material.

Other objects and advantages of the present invention will become apparent from the following description of the preferred embodiments taken in conjunction with the accompanying drawings.

DESCRIPTION OF THE PREFERRED EMBODIMENTS

Figure 1:
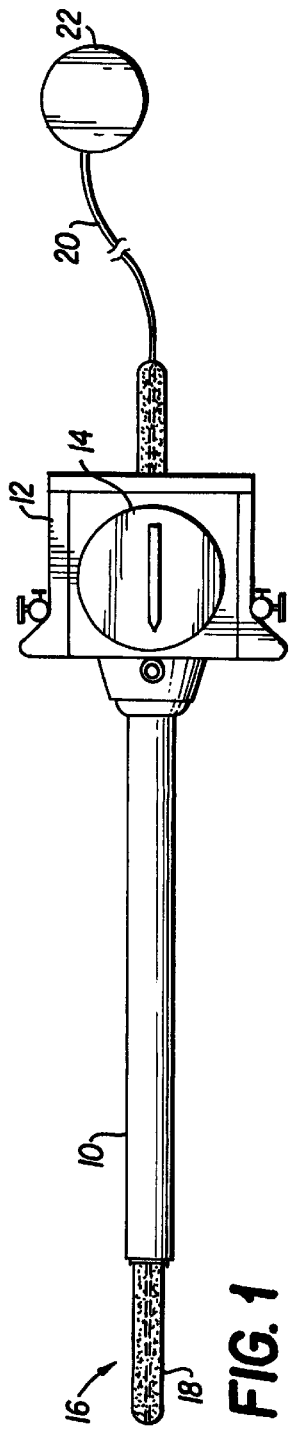
FIG. 1 is a top plan view of a packing device in combination with a trocar sleeve in accordance with the present invention.

A packing device in combination with a trocar sleeve in accordance with the present invention is shown in FIG. 1. The trocar sleeve 10 terminates at its proximal end at a hub 12 having a valve 14 therein forming a passage that can be opened to permit instruments to pass through sleeve 10. The trocar sleeve, hub and valve form a conventional trocar assembly commonly used in laparoscopy wherein a trocar, not shown, passes through sleeve 10 and is used to puncture a pneumoperitoneum and is thereafter withdrawn leaving the sleeve in place to form a portal to gain access to an internal operative site. The valve minimizes loss of inflating fluid. The packing device 16 of the present invention can be used with any type of endoscopic portal providing access to an internal operative site, with or without a sleeve or cannula; and, the trocar sleeve 10 is exemplary only.

Figure 2:
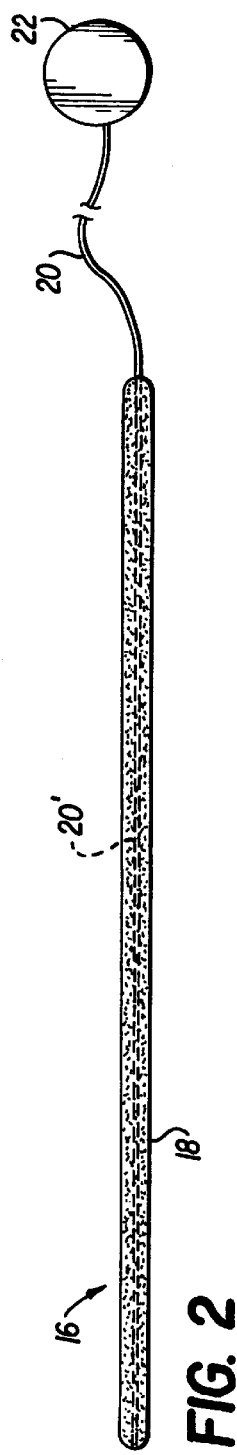
FIG. 2 is a top plan view of a packing device in accordance with the present invention in a dry state.

The packing device 16 is formed of an elongate strip of absorbent, preferably expandable, material 18, as shown in FIG. 2, in a rod-like, relatively straight configuration, attached at a proximal end to a strong, flexible string 20 having an identification tag 22 at its end. The material 18 can be any type of medical grade absorbent material that can absorb body fluids and, preferably, expand from two to four times its size in a dry state, and that is relatively rigid or stiff in the dry state. While an expandable material is preferred to facilitate packing and tissue exposure, if desired, the absorbent material can be non-expandable as long as the material becomes soft and pliant in the wet state after absorption of body fluids. Sponge materials have been found to be the most effective for the packing device, for example, the sponge material utilized in Lamicel osmotic cervical dilators manufactured by Cabot Medical Corporation. In the dry state, the packing device must be sufficiently rigid to allow the packing device to be manipulated in a fashion to be positioned adjacent an operative site to expose and isolate tissue or organ structure to be treated, the rigid nature of the packing device 16 also allowing the packing device to be used to contact and move or position tissue and organ structures to facilitate the procedure to be endoscopically performed. In the dry state, the packing device is essentially a sponge stick. The length and width or lateral size of the packing device will depend upon the procedure to be endoscopically performed; and, as shown in FIG. 1, the packing device has a length longer than the length of the trocar sleeve and hub.

Figure 3:
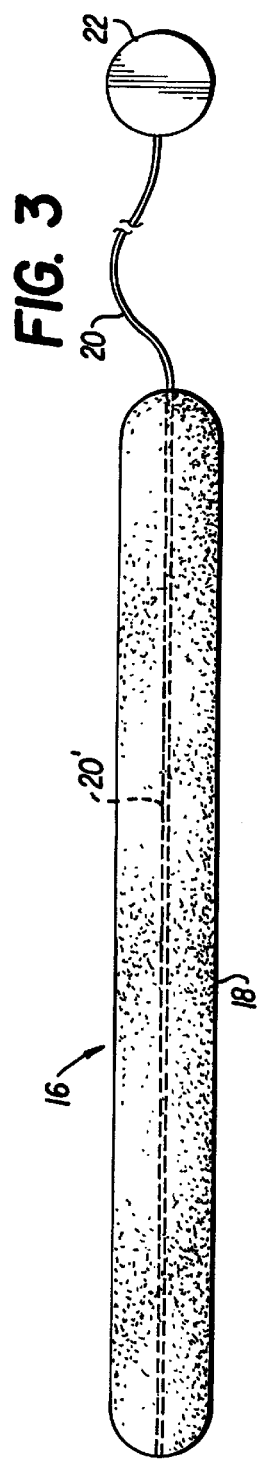
FIG. 3 is a top plan view of the packing device of FIG. 2 in an expanded, wet state.

Once the packing device comes into contact with body fluids, the material 18 will absorb the fluids and expand to a wet state as shown in FIG. 3. In the wet state, the material is soft and flexible facilitating use of the swollen packing device at the operative site.

The construction of the packing device is dependent upon the type of absorbent material employed and the procedure to be performed including the force required to remove the packing device after the procedure is completed. To this end, the string 20 can be suitably attached to the proximal end of the elongate strip of material 18 or the string can pass centrally through the material 18, as shown at 20', to form a core-like support attached to the material along the length thereof. The string should have sufficient tensile strength to prevent breakage of the string when the packing is pulled from the body by grasping the string or tag 22. When the core-like support 20' passes through the material, it can be radiopaque to enhance visualization thereof. The tags 22 can also be radiopaque and, preferably, carry indicia for identifying each packing device, the indicia taking the form of different colors and/or alpha-numeric labeling.

Figure 3A:
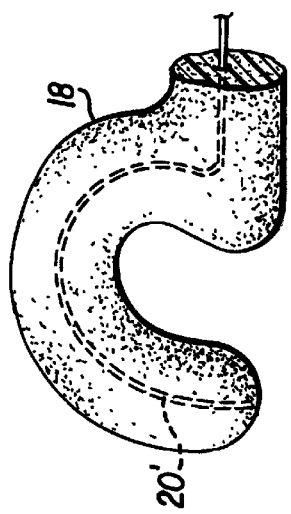
FIGS. 3A and 3B are broken views of the packing device in various configurations in the wet state.
Figure 3B:
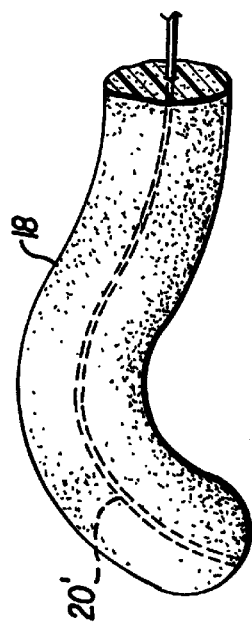

The core-like support 20' can be formed of any suitable material such as string, plastic or metal. In accordance with a particularly advantageous embodiment of the present invention, the core-like support 20' has resilient, spring-like properties and has a normal configuration designed for a particular operative procedure. For example, the core-like support 20' can have the shapes shown in FIGS. 3A or 3B in the normal state. To this end, the core-like support can be made of spring metal to have a curved configuration; and, when the packing device is manufactured, the core-like support is straightened and the absorbent material 18 is attached to the core-like support, for example with adhesive, such that the dry, stiff condition of material 18 maintains the core-like support in a relatively straight configuration. Accordingly, the packing device 16 can be easily inserted through sleeve 10; and, once the packing device is in the body, material 18 will absorb body fluids to become soft and allow the core-like support 20' to return to its normal configuration producing a packing device of predetermined configuration for use in specific procedures. The shape memory of the core-like support can be accomplished in any suitable manner, and support 20' can be disposed within material 18 or externally along an outer edge of material 18.

Figure 4:
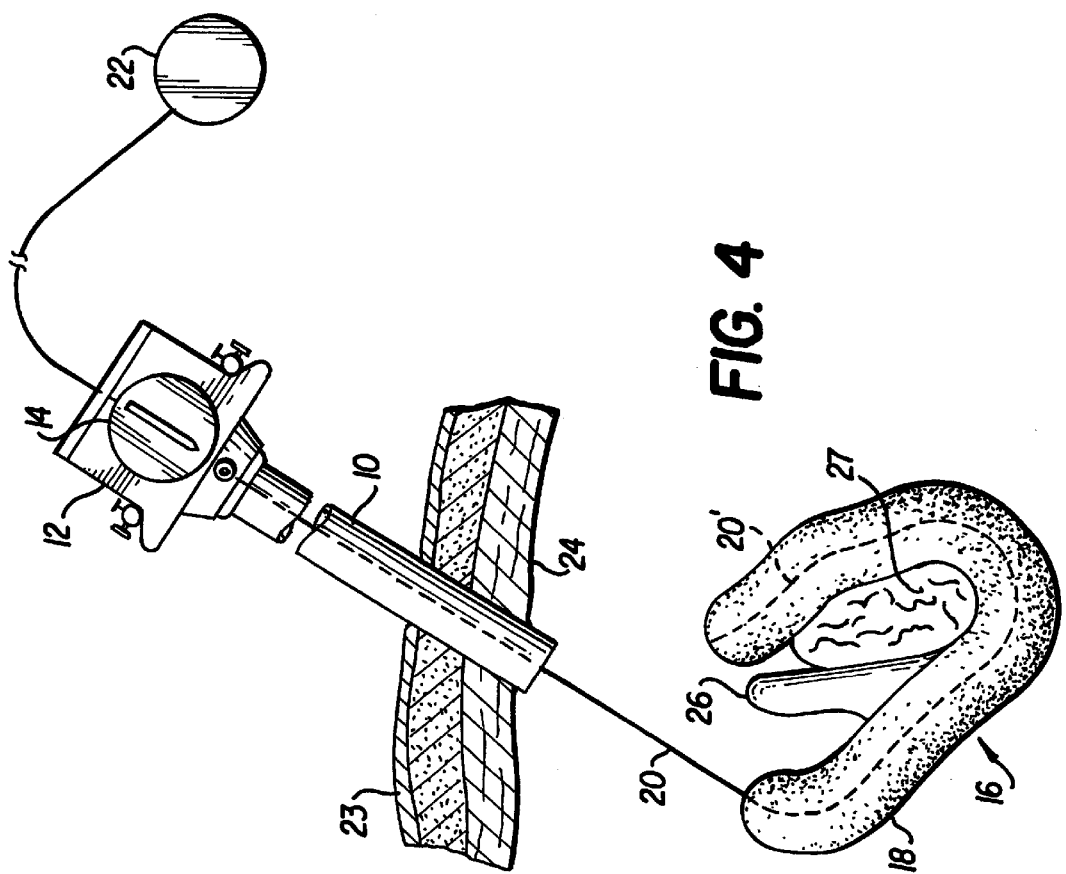
FIG. 4 is a broken view showing a method of endoscopic packing according to the present invention.

In use, after the trocar is withdrawn, the sleeve 10 will provide a portal extending through the skin 23 and the fascia, muscle and anterior peritoneum as shown generally at 24 in FIG. 4. With the sleeve in place, a packing device 16 is passed through the sleeve; and, due to the initial rigidity of the material 18, the packing device can be moved to manipulate tissue to be positioned at the internal operative site to expose the tissue to be treated. As shown in FIG. 4, the packing device 16 is positioned to isolate and expose an appendix 26 to facilitate treatment, such as surgical removal, thereof while protecting surrounding tissue and organ structures, such as the mesentery 27 or the bowel, not shown. Of course, more than one packing device will be used for most procedures, and each packing device will be inserted successively through sleeve 10, or a plurality of sleeves 10, in the manner described above and positioned at the operative site. Since the tag attached to each packing device carries different indicia, specific packing devices can easily be externally, identified. Once the procedure is completed, for example with the use of laser, electrosurgical or mechanical instruments, the sleeve 10 is withdrawn. A single packing device can be withdrawn with the sleeve, and additional packing devices can be withdrawn singly or in pairs dependent upon their expanded, swollen size.

The packing device, along with being effective to absorb body fluids, move or manipulate tissue, expose and isolate tissue to be treated and protect tissue adjacent an operative site, can also be used to collect tissue or fluid for sampling or culture by contacting the tissue or fluid to be sampled with a portion of the packing device in the dry state and then withdrawing the packing device. The dry, medical grade sponge material 18 can be medicated, biodegradable, non-biodegradable, radiopaque and/or culturable for organisms.

Figure 5:
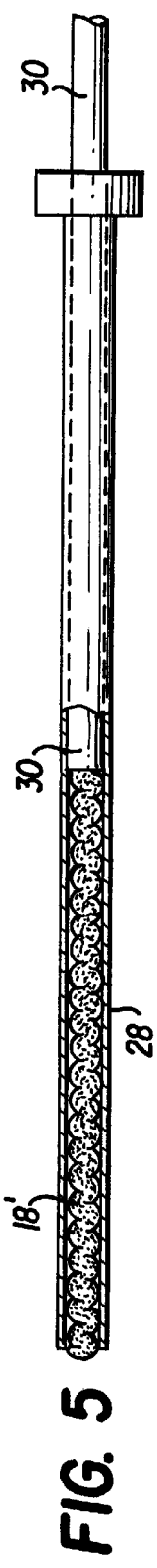
FIGS. 5 and 6 are plan views, partly broken away, of other embodiments of packing devices according to the present invention.
Figure 6:
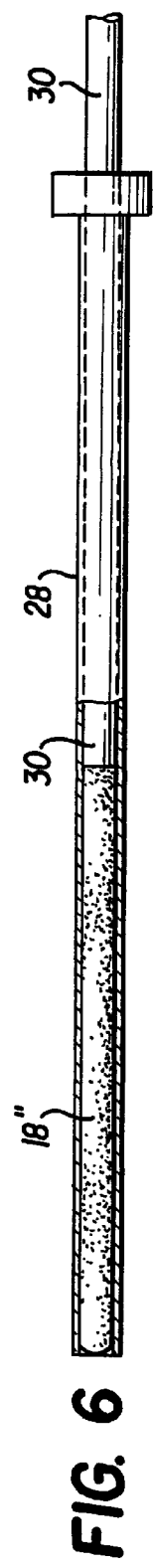

Other embodiments of packing devices according to the present invention are shown in FIGS. 5 and 6. In the embodiment of FIG. 5, a strip of material 18', such as compacted gauze sponge, is disposed in a serpentine or corrugated configuration within a rigid delivery tube 28, and a rod 30 is attached to the proximal end of the material to facilitate deployment and manipulation of the strip of material at the operative site. In the embodiment of FIG. 6, a strip of material 18" is rod shaped, and a rod 30 is attached to the proximal end of the material, the rod 30 and material 18" being disposed within a rigid delivery tube 28 in the same manner as in the embodiment of FIG. 5.

The endoscopic packing system of the present invention as described above permits the expansion of endoscopic procedures to many areas that were previously difficult to reach and visualize and/or dangerous to the patient. For example, the manipulation of the packing device 16 in the dry, stick-like, state acts like a probe allowing the surgeon to see and expose the gall bladder during an endoscopic procedure. The diameter of the packing device will vary in accordance with the procedure to be performed and the size of the portal; and, typically, the packing devices will have diameters of 3 mm, 5 mm, 8 mm and 10 mm. To enhance viewing of the packing device in the body, the material 18 is preferably white in color to provide contrast with the surrounding tissue. Since the packing device is rigid in the dry state, tissue manipulation is enhanced in that initial absorption, softening and expansion occurs only at the portion contacting wet organ structure. Thus, even though the packing device will normally absorb body fluids and soften and expand within a minute of contact, the packing device is particularly effective in exposing and isolating tissue to be treated, and manipulating and protecting tissue.

Figure 7:
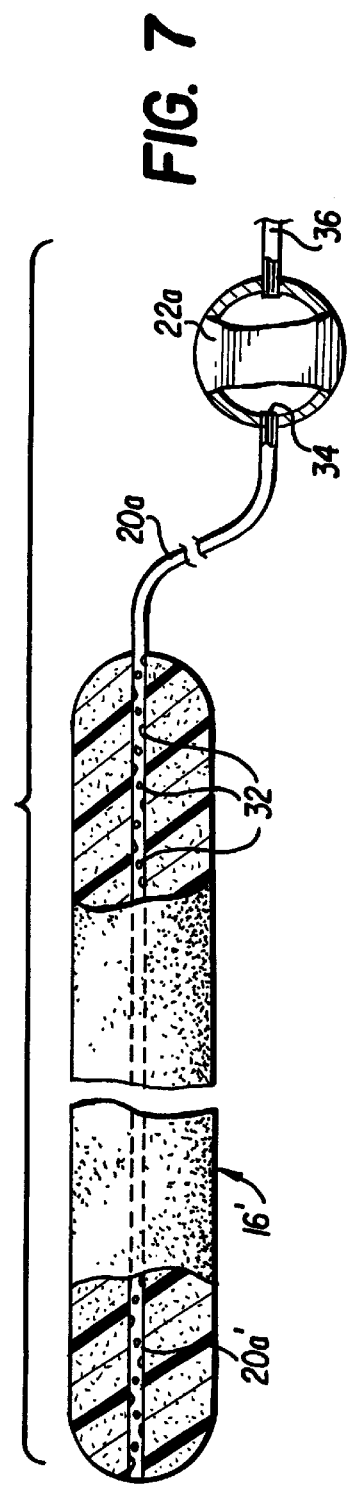
FIG. 7 is a broken view of a further embodiment of a packing device according to the present invention.

A further embodiment of a packing device 16' according to the present invention is shown in FIG. 7 in a wet state. The primary difference between packing device 16' and the previously described packing devices is that the string 20a and the core-like support 20'a are hollow or tubular as is the tag 22a core-like support 20'a has perforations 32 therein. The tag 22a has an inlet 34 communicating with hollow string 20a and an outlet 36 adapted to be connected with a source of suction and/or a drainage collection reservoir. The perforations 32 allow selective or continuous drainage of body fluids through core-like support 20'a and string/tube 20a and tag 22a when the packing device is wet.

Inasmuch as the present invention is subject to many modifications, variations and changes in detail, it is intended that all subject matter discussed above or shown in the illustrative drawings be interpreted as illustrative only and not to be taken in a limiting sense.

What is claimed is:

1. A method of manipulating tissue during an endoscopically performed operative procedure with visualization of an internal operative site through an endoscope comprising the steps of establishing a narrow portal to provide access to the internal operative site;

inserting an elongate device carrying absorbent material at a distal end thereof through the portal; and contacting tissue at the internal operative site with the absorbent material carried at the distal end of the device to manipulate the tissue within the internal operative site.

2. A method of manipulating tissue as recited in claim 1 wherein the device includes a delivery tube and a deployment rod and the absorbent material is disposed at least partially within the delivery tube and has a proximal end attached to the deployment rod, said method further comprising the step of ejecting the absorbent material from the tube by moving the deployment rod.

3. A method of manipulating tissue as recited in claim 1 wherein the device includes an elongate rod attached to the absorbent material and said tissue contacting step includes grasping the rod to move the device to cause the absorbent material to contact and manipulate the tissue.

4. A method of packing during an endoscopically performed operative procedure with visualization of an internal operative site through an endoscope comprising the steps establishing a narrow portal through the skin to provide access to the internal operative site;

inserting an elongate device carrying absorbent material at a distal end thereof through the portal to introduce the absorbent material to the internal operative site; and positioning the absorbent material in contact with tissue at the internal operative site such that at least a portion of the absorbent material absorbs body fluids to facilitate the endoscopically performed operative procedure.

5. A method of manipulating tissue as recited in claim 4 wherein the device includes a delivery tube and a deployment rod and the absorbent material is disposed at least partially within the delivery tube and has a proximal end attached to the deployment rod, and said positioning step includes ejecting the absorbent material from the tube by moving the deployment rod.

6. A method of manipulating tissue as recited in claim 4 wherein the device includes an elongate rod attached to the absorbent material and said positioning step includes grasping the rod to move the device to cause the absorbent material to contact the tissue.

7. A method of performing an endoscopic operative procedure with visualization of an internal operative site through an endoscope comprising the steps of establishing a narrow portal to provide access to the internal operative site;

inserting an absorbent material through the portal to the internal operative site;

positioning the absorbent material at the operative site such that at least a portion of the absorbent material absorbs body fluids; and draining body fluids from the absorbent material for external collection.

\* \* \* \* \*